(12) United States Patent
Bunker (10) Patent No.: US 9,693,975 B2
(45) Date of Patent: *Jul. 4, 2017

(54) BICYCLIC ANALGESIC COMPOUNDS

(71) Applicant: KALYRA PHARMACEUTICALS, INC., San Diego, CA (US)

(72) Inventor: Kevin Duane Bunker, San Diego, CA (US)

(73) Assignee: Kalyra Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,446

(22) Filed: Aug. 17, 2016

(65) Prior Publication Data

US 2016/0355462 A1 Dec. 8, 2016

Related U.S. Application Data

(63) Continuation of application No. 14/199,567, filed on Mar. 6, 2014, now Pat. No. 9,447,025.

(Continued)

(51) Int. Cl.
*C07C 217/52* (2006.01)
*C07C 235/74* (2006.01)
(Continued)

(52) U.S. Cl.
CPC ............ *A61K 31/16* (2013.01); *A61K 9/0014* (2013.01); *A61K 9/0019* (2013.01); *A61K 31/13* (2013.01); *A61K 31/133* (2013.01); *A61K 31/14* (2013.01); *A61K 31/215* (2013.01); *A61K 31/216* (2013.01); *A61K 31/22* (2013.01); *A61K 31/221* (2013.01); *A61K 31/235* (2013.01);
(Continued)

(58) Field of Classification Search
CPC ... C07C 233/06; C07C 233/23; C07C 217/52; C07C 2102/38; A61K 9/0019; A61K 31/216; A61K 31/221; A61K 31/16; A61K 31/24; A61K 45/06
See application file for complete search history.

(56) References Cited

U.S. PATENT DOCUMENTS 5,262,417 A 11/1993 Gammill et al.
5,385,906 A 1/1995 Gammill et al.
(Continued)

FOREIGN PATENT DOCUMENTS

IL 54795 10/1980
WO WO 90/06307 6/1990
(Continued)

OTHER PUBLICATIONS

Adcock ("Transmission of polar substituent effects across the bicyclo[1.1.1]pentane ring system as monitored by 19F NMR shifts" Magnetic Resonance in Chemistry, 2000, 38, p. 115-122).*
(Continued)

*Primary Examiner* — Jafar Parsa
*Assistant Examiner* — Amy C Bonaparte
(74) *Attorney, Agent, or Firm* — Knobbe, Martens, Olson & Bear, LLP (57) ABSTRACT

Analgesic compounds for treatment of pain or fever, comprising a bicyclopentane moiety linked to an amine, combinations of the compounds with opioid analgesic drugs, and methods for treating pain or fever by administering the compounds.

13 Claims, 3 Drawing Sheets

Related U.S. Application Data (60) Provisional application No. 61/781,580, filed on Mar. 14, 2013.

(51) Int. Cl.

| | |
|---|---|
| *C07C 233/06* | (2006.01) |
| *C07C 233/23* | (2006.01) |
| *C07C 211/62* | (2006.01) |
| *C07C 233/41* | (2006.01) |
| *C07C 233/52* | (2006.01) |
| *C07C 233/63* | (2006.01) |
| *A61K 31/16* | (2006.01) |
| *A61K 45/06* | (2006.01) |
| *A61K 31/13* | (2006.01) |
| *A61K 31/14* | (2006.01) |
| *A61K 31/215* | (2006.01) |
| *A61K 31/216* | (2006.01) |
| *A61K 31/235* | (2006.01) |
| *A61K 9/00* | (2006.01) |
| *A61K 31/133* | (2006.01) |
| *A61K 31/22* | (2006.01) |
| *A61K 31/221* | (2006.01) |
| *A61K 31/24* | (2006.01) |

(52) U.S. Cl.
CPC .............. *A61K 31/24* (2013.01); *A61K 45/06* (2013.01); *C07C 211/62* (2013.01); *C07C 217/52* (2013.01); *C07C 233/06* (2013.01); *C07C 233/23* (2013.01); *C07C 233/41* (2013.01); *C07C 233/52* (2013.01); *C07C 233/63* (2013.01); *C07C 235/74* (2013.01); *C07C 2102/38* (2013.01)

(56) References Cited

U.S. PATENT DOCUMENTS

| | | | |
|---|---|---|---|
| 8,846,698 | B2 | 9/2014 | Andrews et al. |
| 9,326,973 | B2 | 5/2016 | Hewawasam et al. |
| 9,447,025 | B2 * | 9/2016 | Bunker .................. A61K 45/06 |
| 9,447,026 | B2 * | 9/2016 | Bunker .................. A61K 45/06 |
| 2013/0029987 | A1 | 1/2013 | Bennett et al. |
| 2014/0275245 | A1 | 9/2014 | Bunker |
| 2016/0016892 | A1 | 1/2016 | Bunker |
| 2016/0075654 | A1 | 3/2016 | Bunker et al. |

FOREIGN PATENT DOCUMENTS

| | | |
|---|---|---|
| WO | WO 2009/153720 | 12/2009 |
| WO | WO 2012/137089 | 10/2012 |
| WO | WO 2012/145569 | 10/2012 |
| WO | WO 2013/024895 | 2/2013 |
| WO | WO 2013/126856 | 8/2013 |
| WO | WO 2014/149819 | 9/2014 |
| WO | WO 2015/089170 | 6/2015 |
| WO | WO 2015/134710 | 9/2015 |

OTHER PUBLICATIONS

Contreras ("Influence of sigma-hyperconjugative interactions on 13C substituent chemical shifts: experimental and theoretical study in 1—X,3—CH3-bicyclo[1.1.1]pentanes" Magnetic Resonance in Chemistry, 2004, 42, p. S202-S206).*
Bunz ("Bridgehead-coupled bicycle[1.1.1]pentanes: synthesis and structure" Chemische Berichte, 1988, 121, p. 1785-90).*
Adcock, W., "A DFT-GIAO and DFT-NBO study of polar substituent effects on NMR $^{17}$O chemical shifts in some rigid polycyclic alkanes" *J. Phys. Org. Chem.* (2011) 24:492-498.
Adcock, W., et al., "Polar Substituent Effects in the Biocyclo[1.1.1]pentane Ring System: Acidities of 3-Substituted Biocyclo[1.1.1]pentane-1-carboxylic Acids" *J. O. Chem.* (2005) 70(3):1029-1034.
Adcock, W., et al., "Computation and analysis of 19F substituent chemical shifts of some bridgehead-substituted polycyclic alkyl fluorides" *Magn. Reson. Chem.* (2003) 41(7):503-508.
Adcock, W., et al., "Transmission of polar substituent effects across the bicycle[1.1.1]pentane ring system as monitored by $^{19}$F NMR shifts" *Magn. Reson. Chem.* (2000) 38:115-122.
Annese, C., et al., "Oxyfunctionalization of Non-Natural Targets by Dioxiranes. 6. On the Selective Hydroxylation of Cubane" *Org. Lett.* (2009) 11(16):3574-3577.
Applequist, D.E., et al., "Polar Substituent Effects in 1,3-Disubstituted Bicyclo[1.1.1]pentanes" *J. Org. Chem.* (1982) 47:4985-4995.
Arnone A., et al., "Highly Enantiospecific Oxyfunctionalization of Nonactivated Hydrocarbon Sites by Perfluoro-cis-2-*n*-butyl-3-*n*-propyloxaziridin" *Org. Lett.* (1999) 1(2):281-284.
Asensio, G., et al., "Regioselective Oxyfunctionalization of Unactivated Tertiary and Secondary C—H Bonds of Alkylamines by Methyl(trifluoromethyl)dioxirane in Acid Medium" *J. Am. Chem. Soc.* (1993) 115:7250-7253.
Bioreversible Carriers in Drug Design: Theory and Application 13-21 and Table of Contents (E. B. Roche ed., Pergamon Press New York 1987).
Cao K. et al., "Carbon-14 labeling of Saxagliptin (BMS-477118)" *J Label Compd Radiopharm* (2007) 50:1224-1229.
Contreras, R.H. et al., "Experimental and DFT studies on the transmission mechanisms of analogous NMR $J_{CH}$ and $J_{CC}$ couplings in 1-X-and 1-X-3-methylbicyclo[1.1.1]-pentanes" *Magn. Reson. Chem.* (2007) 45:572-577.
Dasgupta A., et al., "Interaction of White and Pink Grapefruit Juice with Acetaminophen (Paracetamol) In Vivo in Mice" *J. Med. Food* (2008) 11(4):795-798.
Design of Prodrugs (Hans Bundgaard ed., Elsevier 1985) Table of Contents only.
Henry, J., "Future Basic Science Directions Into Mechanisms of Neuropathic Pain" Orofac. Pain (2004) 18:306-310.
Janecki, T., et al., "[n]Staffanes with Terminal Nitrile and Isonitrile Functionalities and their Metal Complexes" *Collect. Czech. Chem. Commun.* (1993) 83:89-104.
Jasys, V. J., et al., "Preparation of Fluoroadamantane Acids and Amines: Impact of Bridgehead Fluorine Substitution on the Solution- and Solid-State Properties of Functionalized Adamantanes" *J. Am. Chem. Soc.* (2000) 122:466-473.
Khusnutdinov, R. I., et al., "Selective Hydroxylation of Adamantane and Its Derivatives" *Russian Journal of Organic Chemistry* (2009) 45(8):1137-1142.
Komiya, N., et al., "Ruthenium-catalysed oxidation of alkanes with peracetic acid in trifluoroacetic acid: ruthenium as an efficient catalyst for the oxidation of unactivated C—H bonds" *Chem. Commun.* (2001):65-66.
Lee, S. et al., "Chemospecific Chromium[VI] Catalyzed Oxidation of C—H Bonds at 40 °C" *J. Am. Chem. Soc.* (2002) 124:13978-13979.
Lee, I., et al., "Effects of Different Concentrations and Volumes of Formalin on Pain Response in Rats" (2000) Anaesthesiologica sinica, 38:59-64.
Linz, T., et al., "Oxidation of Non-Activated C—H Bonds in Hydrocarbons and Steroids" *Tetrahedron Letters* (1987) 28(52):6581-6582.
McNeill, E. et al., "Ruthenium-Catalyzed Hydroxylation of Unactivated Tertiary C—H Bonds" *J. Am. Chem. Soc.* (2010) 132:10202-10204.
McNeill, E. et al., "Catalytic C—H oxidation by a triazamacrocyclic ruthenium complex" *Chem. Sci.* (2012) 3:1810-1813.
Onomura, O., et al., "Efficient Oxidation of Adamantanes by Sodium Nitrite with Molecular Oxygen in Trifluoroacetic Acid" *Synlett*, (2006) 15:2415-2418.
Pätzel, M., et al., "3-Aminobicyclo[1.1.1]pentane-1-carboxylic Acid Derivatives: Synthesis and Incorporation into Peptides" *Eur. J. Org. Chem.* (2004):493-498.

(56) References Cited

OTHER PUBLICATIONS

Pritz, S., et al., "Synthesis of a chiral amino acid with bicycle[1.1.1]pentane moiety and its incorporation into linear and cyclic antimicrobial peptides" *Org. Biomed. Chem.* (2007) 5:1789-1794.

Pro-drugs as Novel Delivery Systems (T. Higuchi and V. Stella eds., vol. 14 A.C.S. Symposium Series, American Chemical Society 1975) Table of Contents and Forward only.

Shmailov, A., et al., "Synthesis of functionalized 5-(3-R-1-admantyl)uracils and related compounds" *Tetrahedron* (2010) 66:3058-3064.

Shmailov, A., et al., "First synthesis of α-(3-R-1-adamantyl)sulfoacetic acids and their derivatives" *Tetrahedron* (2012) 68:4765-4772.

Siegers, C.P., "Relations between Hepatotoxicity and Pharmacokinetics of Paracetamol in Rats and Mice" *Pharmacology* (1978) 16:273-278.

Sorochinsky A. E., et al., "Regioselective Oxyfunctionalization of Bridgehead Adamantane Derivatives" *Tetrahedron* (1997) 53(7):5995-6000.

Stepan, A., et al., "Application of the Bicyclo[1.1.1]pentane Motif a Nonclassical Phenyl Ring Bioisostere in the Design of a Potent and Orally Active γ-Secretase Inhibitor" *J. Med. Chem.* (2012) 55:3414-3424.

Sufka, K., et al., "Scoring the mouse formalin test: validation study" Eur. J. Pain (1998) 2:351-358.

Tanemura, K., et al., "Formation of adamantan-1-ols by the reactions of adamantanes with 2,3-dichloro-5,6-dicyano-*p*-benzoquinone (DDQ) in trifluoromethanesulfonic acid" *J. Chem. Soc., Perkin Trans.* 1 ( 2001) 1: 3230-3231.

Tjølsen, A., et al, "The formalin test: an evaluation of the method" (1992) Pain, 51:5-17.

Toops, D., et al., "Efficient Synthesis of 1-(Trialkylstannyl)-and 1-(Triarylstannyl)biocyclo[1.1.1]pentanes" *J. Org. Chem.* (1993) 58:6505-6508.

Vahidy, W., et al, "Effects of intracerebroventricular injections of free fatty acids, lysophospholipids, or platelet activating factor in a mouse model of orofacial pain" (2006) Exp. Brain Res. 174:781-785.

Vissers, K., et al, "Pharmacological correlation between the formalin test and the neuropathic pain behavior in different species with chronic construction injury" Pharmacology, Biochemistry and Behavior (2006) 84:479-486.

Wanka, L., et al., "γ-Aminoadamantanecarboxylic Acids Through Direct C—H Bond Amidations" *Eur. J. Org. Chem.* (2007) 2007(9):1474-1490.

Wheeler-Aceto, H., et al., "Standardization of the rat paw formalin test for the evaluation of analogesics" Psychopharmacology (Berl) (1991) 104:35-44.

Zarubaev V. V. et al., "Synthesis of anti-viral activity of azolo-admantanes against influenza A virus" *Bioorganic & Medicinal Chemistry* (2010) 18:839-848.

Zehnder et al., "Optimization of Potent, Selective, and Orally Bioavailable Pyrrolodinopyrimidine-Containing Inhibitors o Heat Shock Protein 90. Identification of Development Candidate 2-Amino-4-{4-chloro-2-[2-(4-fluoro-1*H*-pyrazol-1-yl)ethoxy]-6-methylphenyl}-*N*-(2,2-difluoropropyl)-5,7-dihydro-6H-pyrrolo[3,4-*d*]pyrimidine-6-carboxamidef" J. Med. Chem. (2011) 54:3368-3385.

Office Action dated Jan. 15, 2016 for U.S. Appl. No. 14/439,636, filed Apr. 29, 2015.

International Search Report and Written Opinion dated May 19, 2014 for PCT Application No. PCT/US2014/021038, filed Mar. 6, 2014.

International Preliminary Report on Patentability dated Feb. 24, 2015 for PCT Application No. PCT/US2014/021038, filed Mar. 6, 2014.

Office Action dated Sep. 17, 2015 for U.S. Appl. No. 14/199,567, filed Mar. 6, 2014.

Office Action dated Jan. 20, 2016 for U.S. Appl. No. 14/199,567, filed Mar. 6, 2014.

Advisory Action dated Mar. 28, 2016 for U.S. Appl. No. 14/199,567, filed Mar. 6, 2014.

Extended European Search Report dated Oct. 19, 2016 for EP Application No. 14769979.7, filed Oct. 4, 2015.

Bunz et al., Chemische Berichte (1998) 121(10):1785-1790 (RN 115092-76-7 and RN 115092-79-0).

Hassner, A. "e-EROS Encyclopedia of Reagents for Organic Chemistry" (2005) 1-6 (John Wiley & Sons, Ltd., Chichester) (RN 351882-60-5 and RN351882-61-6).

Wang et al., "The Oral Analgesic Efficacy of Bicifadine Hydrochloride in Postoperative Pain" J Clin Pharmacol (1982) 22:160-164.

\* cited by examiner

BICYCLIC ANALGESIC COMPOUNDS

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57, such as U.S. application Ser. Nos. 14/199,567, filed Mar. 6, 2014 and 61/781,580, filed Mar. 14, 2013.

BACKGROUND

Field

This disclosure relates to small molecule drugs typified by a bicyclic aliphatic group. The disclosed compounds include analgesic compounds and antipyretic compounds. Also disclosed are methods of synthesis, drug combinations, and medical uses.

Description

Nonsteroidal anti-inflammatory compounds, or NSAIDs, are an extremely useful group of small molecule drugs, typified by acetylsalicylic acid, ibuprofen, and naproxen. These are often sold without prescription, and are variously used to treat pain, inflammation, and fever. However, NSAIDs can have undesirable side effects, including gastric upset or gastric bleeding.

Acetaminophen, also known as paracetamol or APAP, is also an effective pain reliever often sold over the counter (without prescription). Although it shares analgesic and antipyretic properties with NSAIDs, it has only weak anti-inflammatory properties, and is thus not an NSAID. Unlike many NSAIDs, acetaminophen does not cause gastric upset or bleeding in prescribed doses. Thus, it is an extremely useful drug for those wishing analgesia without adverse gastric side effects.

Acetaminophen is often combined with other drugs for relief of symptoms of influenza and the common cold, among other indications. It is particularly useful in combination with opioid analgesics, where it exhibits synergistic analgesic properties and allows patients to achieve adequate pain relief with lower doses of opioids. The most widely prescribed drug in the United States is a combination of acetaminophen and hydrocodone, with over 130 million prescriptions in the year 2010. Other acetaminophen-opioid combinations, including combinations with oxycodone, are also widely prescribed.

Acetaminophen poisoning is the most common cause of acute liver failure in the Western world, and acetaminophen accounts for the most drug overdoses in the English-speaking world. Acetaminophen is metabolized to form N-acetyl-p-benzoquinoneimine (NAPQI), which depletes glutathione in the liver and injures hepatocytes, leading to acute liver failure and often death. The acetaminophen-opioid combination drugs are commonly implicated in such toxicity, for various reasons. First, patients might not recognize that the prescribed pain relievers contain acetaminophen, and may supplement with acetaminophen if pain relief is inadequate. Second, continued administration of opioids can lead to tolerance and the need for increased dosages to obtain a comparable opioid effect, and users or abusers of the combination drugs may exceed safe dosages of acetaminophen as a consequence.

This has led the U.S. FDA to seek reduced amounts of acetaminophen in the opioid combination drugs and has also led an FDA advisory panel to recommend banning such drugs all together. Although the acetaminophen-opioid drugs remain on the market, there is a strong need for a less toxic replacement without the same hepatotoxicity risks.

Acetaminophen has the structure:

Acetaminophen

Acetaminophen is metabolized in vivo to form the hepatotoxic compound N-acetyl-p-benzoquinoneimine:

N-acetyl-p-benzoquinoneimine

SUMMARY

Disclosed are compounds having analgesic properties that do not form benzoquinoneimine metabolites and, thus, avoid the hepatotoxicity mechanism of acetaminophen. These include compounds of Formula 1:

Formula 1 wherein $R^1$ is H, —CH$_3$, CF$_3$, or (C$_2$ to C$_5$) substituted or unsubstituted lower alkyl;

$R^2$ is H or C(=Y)R$^4$;

$R^3$ is H, F, D, hydroxy, (C$_1$ to C$_{10}$) alkoxy, (C$_1$ to C$_{30}$) substituted or unsubstituted alkyl, aryl, alkenyl, alkynyl, cycloalkyl, cycloalkenyl, cycloalkynyl, heterocycle, heteroaryl, arylalkyl, alkylaryl, heteroarylalkyl, or —(C=O)L;

$R^4$ is CF$_3$ or (C$_1$ to C$_{10}$) substituted or unsubstituted lower alkyl;

Y is S or O; and (C=O)L is a hydrolyzable prodrug ester leaving group. In some embodiments, L is a substituted or unsubstituted alkyl, cycloalkyl, aryl, alkenyl, alkynyl, cycloalkyl, cycloalkenyl, cycloalkynyl, heterocycle, heteroaryl, arylalkyl, alkylaryl, heteroarylalkyl, or any combination of such groups, all of which may be substituted or unsubstituted and which may range from $C_1$ to $C_{30}$ or otherwise include from 1 to 30 atoms, excluding hydrogen.

In some embodiments, L has the structure —$CH_3$, $CH_2CH_3$, $CH_2CH_2OH$,

, or

DETAILED DESCRIPTION

Embodiments of the present compounds include a core structure having a bicyclo[1.1.1]pentane group. It should be noted that due to valence considerations, it is impossible to connect a substituent through a double bond (such as a carbonyl or imine group) at either end of bicyclo[1.1.1] pentane (i.e., at the 1 or 3 positions). Thus, likely metabolic products of the compounds disclosed herein do not include analogs of benzoquinoneimine, and thus do not present a hepatotoxicity risk through the NAPQI mechanism.

Definitions:

As used herein, the term "alkyl" refers to a fully saturated aliphatic hydrocarbon group. The alkyl moiety may be branched or straight chain. Examples of branched alkyl groups include, but are not limited to, isopropyl, sec-butyl, t-butyl and the like. Examples of straight chain alkyl groups include, but are not limited to, methyl, ethyl, propyl, butyl, pentyl, hexyl, heptyl, and the like.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. An example of an optional substituent includes, but is not limited to, oxo (═O).

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NHMethyl, —$NH_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pro-drug ester" refers to derivatives of the compounds disclosed herein formed by the addition of any of several ester-forming groups that are hydrolyzed under physiological conditions. Examples of pro-drug ester groups include, but are not limited to fatty acid esters, pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The abbreviation ($C_n$) in conjunction with the name of a chemical group (e.g., alkyl) refers to the number of carbon atoms in that group. Thus, the term ($C_1$-$C_5$) alkyl means an alkyl group having 1 to 5 carbon atoms.

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and pro-drug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

As used herein, "pharmaceutically acceptable" refers to a material that is not biologically or otherwise undesirable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition or who displays one or more of its symptoms. An effective amount may completely or partially prevent the occurrence or recurrence of the disease or condition or symptom thereof and/or may be therapeutic in terms of a partial or complete cure for the disease or condition and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to acetaminophen (e.g., pain, fever, inflammation, ischemic injury (such as myocardial and/or cerebral), or neuronal injury). In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/ prevented (e.g., the type of pain), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and an acetaminophen prodrug may be considered to be given in an effective amount if, in conjunction with one or more additional pharmaceutical agents, one or more desirable or beneficial result(s) may be or are achieved.

When used with respect to methods of treatment and/or prevention and the use of the compounds of Formula 1 described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.).

Compounds of Formula 1 will now be further described:

Formula 1 wherein $R^1$ is H, —$CH_3$, $CF_3$, or ($C_2$ to $C_5$) substituted or unsubstituted lower alkyl;

$R^2$ is H or C(=Y)$R^4$;

$R^3$ is H, hydroxy, ($C_1$ to $C_{10}$) alkoxy, or —O(C=O)L,

$R^4$ is $CF_3$ or ($C_1$ to $C_{10}$) substituted or unsubstituted lower alkyl;

Y is S or O; and

(C=O)L is a hydrolyzable prodrug ester leaving group.

In some embodiments, L is a substituted or unsubstituted alkyl, aryl, alkenyl, heterocycle, heteroaryl, arylalkyl, alkylaryl, heteroarylalkyl, or any combination of such groups, all of which may be substituted or unsubstituted and which may range from $C_1$ to $C_{30}$ or otherwise include from 1 to 30 atoms, excluding hydrogen.

In some embodiments, L has the structure —$CH_3$, $CH_2CH_3$, $CH_2CH_2OH$,

Particular nonlimiting embodiments of the compounds of Formula 1 include the following:

1

2

3

4

Figure 1:
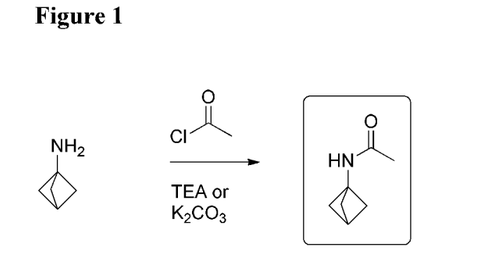
FIG. 1 illustrates a synthetic pathway for creating a bicyclo[1.1.1]pentyl amide compound.
Figure 2:
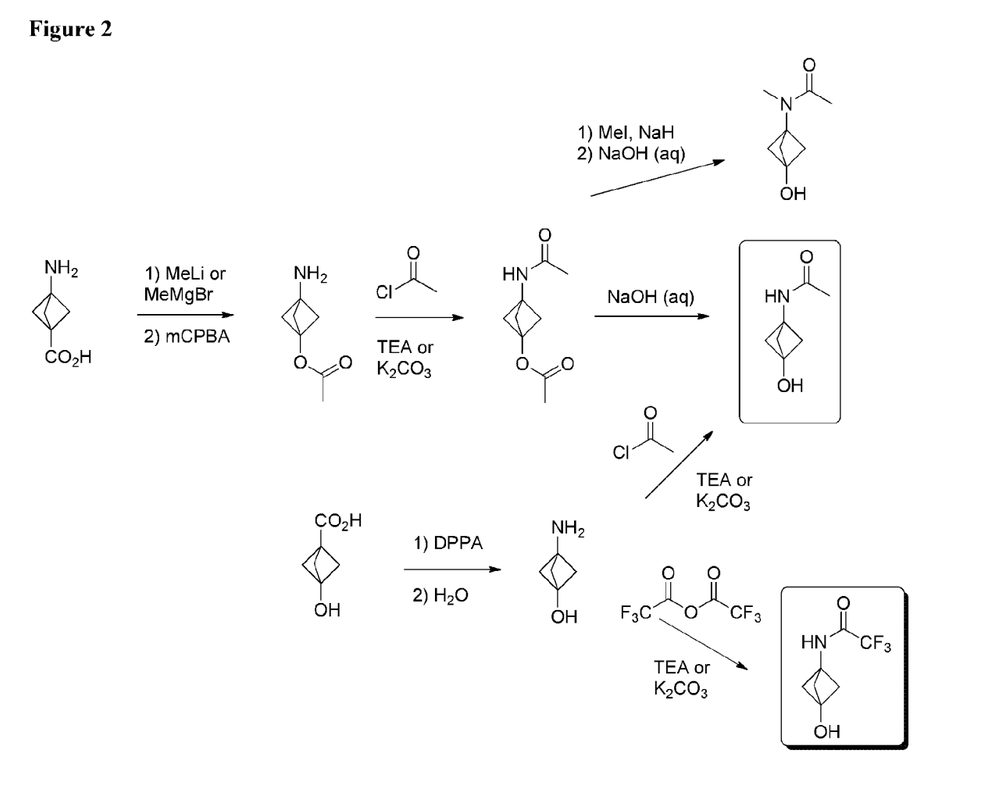
FIG. 2 illustrates a synthetic pathway for creating hydroxy bicyclo[1.1.1]pentyl amide compounds.
Figure 3:
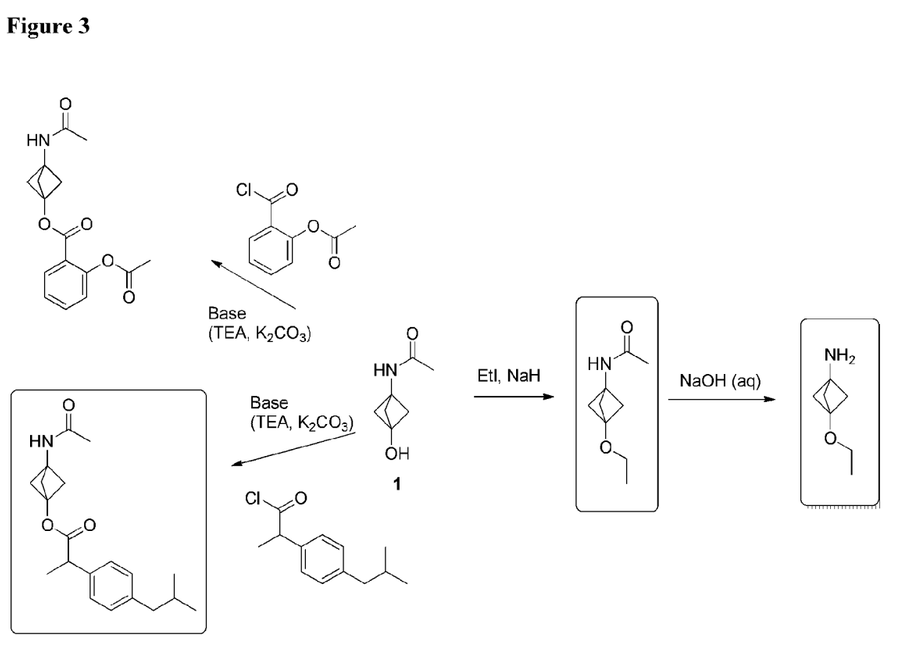
FIG. 3 illustrates a synthetic pathway for creating analgesic ethers and prodrug esters of bicyclo[1.1.1]pentyl compounds.

Synthesis:

The various analgesic compounds contemplated herein can be synthesized from known starting materials by various routes. Some suitable routes are illustrated in FIGS. 1-3, with syntheses described in more detail in the following description and Examples.

Scheme 1

The commercially available 3-aminobicyclo[1.1.1]pentane-1-carboxylic acid can be converted to the methyl ketone intermediate by treatment with either methyl lithium or methylmagnesium bromide (Scheme 1). Baeyer-Villager type oxidation with mCPBA or other peroxycarboxylic acids can give 3-aminobicyclo[1.1.1]pentan-1-yl acetate. The amine can then be coupled with an appropriate carboxylic acid or acid chloride, such as acetyl chloride to give 3-acetamidobicyclo[1.1.1]pentan-1-yl acetate (3). Selective hydrolysis of the ester group with hydroxide ion gives N-(3-hydroxybicyclo[1.1.1]pentan-1-yl)acetamide (1). Alternatively, starting with the commercially available 3-hydroxybicyclo[1.1.1]pentane-1-carboxylic acid and carrying out a Curtius reaction or modified Curtius reaction using diphenylphosphoryl azide gives the amino alcohol intermediate, which can then be treated with acetyl chloride (1 eq) in the presence of base (for example, $K_2CO_3$, $Na_2CO_3$, TEA, and the like) to give N-(3-hydroxybicyclo[1.1.1]pentan-1-yl)acetamide (1) or with acetyl chloride (>2 eq) in the presence of base (for example, $K_2CO_3$, $Na_2CO_3$, TEA, and the like) to give 3-acetamidobicyclo[1.1.1]pentan-1-yl acetate (3).

Scheme 2

4

The commercially available bicyclo[1.1.1]pentan-1-amine can be coupled with an appropriate carboxylic acid or acid chloride, such as acetyl chloride in the presence of base (for example, $K_2CO_3$, $Na_2CO_3$, $NaHCO_3$, TEA, pyridine, and the like) to give N-(bicyclo[1.1.1]pentan-1-yl)acetamide (4) (Scheme 2).

C—H activation or oxidation reagents are described in the following references, which are hereby incorporated by reference in their entirety: $H_2SO_4$ (conc.)/$HNO_3$ (conc. or 50%) [Cao K. et al., *J Label Compd Radiopharm* 2007; 50: 1224-1229; Wanka, L., et al., *Eur. J. Org. Chem.* 2007, 1474-1490]; $H_2SO_4$ (conc.)/$NH_4NO_3$ [Zarubaev V. V. et al., *Bioorganic & Medicinal Chemistry* 18 (2010) 839-848]; perfluoro-cis-2-n-butyl-3-n-propyloxaziridine [Sorochinsky A. E., et al., *Tetrahedron*, 1997, 53, 5995-6000; Arnone A., et al., *Org. Lett.*, 1999, 1, 281-284]; $CBr_4/H_2O/Mo(CO)_6$ [Khusnutdinov, R. I., et al., *Russian Journal of Organic Chemistry*, 2009, 45, 1137-1142]; [(Me$_3$tacn)RuCl$_3$], CAN, AgClO$_4$, t-BuOH/H$_2$On [McNeill, E., Du Bois, J., *Chem. Sci.*, 2012, 3, 1810-1813]; RuCl$_3$·xH$_2$O, KBrO$_3$, H$_2$O, pyridine, CH$_3$CN [McNeill, E., Du Bois, J., *J. Am. Chem. Soc.*, 2010, 132, 10202-10204]; dimethyldioxirane (DMD) or methyl(trifluoromethyl)dioxirane (TFDO), with or without HBF$_4$ [Annese, C., et al., *Org. Lett.*, 2009, 11, 3574-3577; Asensio, G., et al., *J. Am. Chem. Soc.* 1993, 115, 1250-7253]; CrO$_3$, H$_5$IO$_6$ [Lee, S., Fuchs, P. L., *J. Am. Chem. Soc.* 2002, 124, 13978-13979]; KMnO$_4$, KOH [Jasys, V. J., et al., *J. Am. Chem. Soc.*, 2000, 122, 466-473]; H$_2$SO$_4$ (conc.), (CF$_3$CO)$_2$O [Shmailov, A., et al., *Tetrahedron*, 2010, 66, 3058-3064; Shmailov, A., et al., *Tetrahedron*, 2012, 68, 4765-4772]; NaNO$_2$, TFA, O$_2$ [Onomura, O., et al., *Synlett*, 2006, 2415-2418]; CrO$_3$, CH$_3$CO$_2$H, (H$_3$CO)$_2$O [Linz, T., Schäfer, H. J., *Tetrahedron Letters*, 1987, 28, 6581-6582]; RuCl$_3$ (cat.), TFA, DCM, peracetic acid [Komiya, N., et al., *Chem. Commun.*, 2001, 65-66]; DDQ, TfOH [Tanemura, K., et al., *J. Chem. Soc., Perkin Trans. 1*, 2001, 3230-3231].

The C—H activation/oxidation (Scheme 3) of commercially available bicyclo[1.1.1]pentan-1-amine by an appropriate oxidizing reagent or condition (for example, $H_2SO_4$ (conc.)/$HNO_3$ (conc. or 50%); $H_2SO_4$ (conc.)/$NH_4NO_3$; perfluoro-cis-2-n-butyl-3-n-propyloxaziridine; $CBr_4/H_2O/Mo(CO)_6$; [(Me$_3$tacn)RuCl$_3$], CAN, AgClO$_4$, t-BuOH/H$_2$O; RuCl$_3$·xH$_2$O, KBrO$_3$, H$_2$O, pyridine, CH$_3$CN; dimethyldioxirane (DMD) or methyl(trifluoromethyl)dioxirane (TFDO), with or without HBF$_4$; CrO$_3$, H$_5$IO$_6$; KMnO$_4$, KOH; and the like) can give 3-aminobicyclo[1.1.1]pentan-1-ol. The amino alcohol intermediate can then be coupled with an appropriate carboxylic acid or acid chloride, such as acetyl chloride to give 3-acetamidobicyclo[1.1.1]pentan-1-yl acetate (3). Selective hydrolysis of the ester group with hydroxide ion gives N-(3-hydroxybicyclo[1.1.1]pentan-1-yl)acetamide (1). Alternatively, starting with N-(bicyclo[1.1.1]pentan-1-yl)acetamide (4), C—H activation/oxidation with an appropriate oxidizing reagent or conditions (for example, see listed above, and $H_2SO_4$ (conc.), (CF$_3$CO)$_2$O; NaNO$_2$, TFA, O$_2$; CrO$_3$, CH$_3$CO$_2$H, (H$_3$CO)$_2$O; RuCl$_3$ (cat.), TFA, DCM, peracetic acid; DDQ, TfOH; and the like) can give N-(3-hydroxybicyclo[1.1.1]pentan-1-yl)acetamide (1).

Scheme 4

The treatment of N-(3-hydroxybicyclo[1.1.1]pentan-1-yl) acetamide (1) with ethyl iodide in the presence of a base (such as NaHCO₃, Na₂CO₃, TEA, pyridine, NaH, and the like) gives N-(3-ethoxybicyclo[1.1.1]pentan-1-yl)acetamide (2) (Scheme 4).

Scheme 5

Hydrolysis of N-(3-ethoxybicyclo[1.1.1]pentan-1-yl)acetamide (2) with sodium hydroxide (or basic aqueous conditions) gives 3-ethoxybicyclo[1.1.1]pentan-1-amine (6) (Scheme 5).

Scheme 6

The treatment of 3-aminobicyclo[1.1.1]pentan-1-yl acetate (prepared as depicted in Scheme 1) with methyl iodide in the presence of base leads to 3-(methylamino) bicyclo[1.1.1]pentan-1-yl acetate, followed by hydrolysis with aqueous hydroxide gives 3-(methylamino)bicyclo [1.1.1]pentan-1-ol (Scheme 6). The amino alcohol intermediate can be coupled with an appropriate carboxylic acid or acid chloride, such as acetyl chloride in the presence of base (for example, K₂CO₃, Na₂CO₃, NaHCO₃, TEA, pyridine, NaH, and the like) to give N-(3-hydroxybicyclo[1.1.1]pentan-1-yl)-N-methylacetamide (5).

Scheme 7

The treatment of 3-aminobicyclo[1.1.1]pentan-1-ol with trifluoroacetic anhydride in the presence of base (for example, K₂CO₃, Na₂CO₃, NaHCO₃, TEA, pyridine, and the like) gives 2,2,2-trifluoro-N-(3-hydroxybicyclo[1.1.1] pentan-1-yl)acetamide (7) (Scheme 7).

Scheme 8

The treatment of N-(3-hydroxybicyclo[1.1.1]pentan-1-yl) acetamide (1) with O-acetylsalicyloyl chloride in the presence of a base (for example, K$_2$CO$_3$, Na$_2$CO$_3$, NaHCO$_3$, TEA, pyridine, and the like) gives 3-acetamidobicyclo [1.1.1]pentan-1-yl 2-acetoxybenzoate (8) (Scheme 8). Alternatively, the coupling of N-(3-hydroxybicyclo[1.1.1]pentan-1-yl)acetamide (1) with O-acetylsalicylic acid in the presence of a coupling agents (for example, HATU, EDCI, HOBt, HOAt, CDI, DCC, TP$_3$, isobutyl chloroformate, and the like) gives 3-acetamidobicyclo[1.1.1]pentan-1-yl 2-acetoxybenzoate (8). Additionally, the treatment of N-(3-hydroxybicyclo[1.1.1]pentan-1-yl)acetamide (1) with 2-(4-isobutylphenyl)propanoyl chloride in the presence of a base (for example, K$_2$CO$_3$, Na$_2$CO$_3$, NaHCO$_3$, TEA, pyridine, and the like) gives 3-acetamidobicyclo[1.1.1]pentan-1-yl 2-(4-isobutylphenyl)propanoate (9) (Scheme 8). Alternatively, the coupling of N-(3-hydroxybicyclo[1.1.1]pentan-1-yl)acetamide (1) with (±)-2-(4-isobutylphenyl)propanoic acid in the presence of a coupling agents (for example, HATU, EDCI, HOBt, HOAt, CDI, DCC, TP$_3$, isobutyl chloroformate, and the like) gives 3-acetamidobicyclo [1.1.1]pentan-1-yl 2-(4-isobutylphenyl)propanoate (9).

Formulation and Administration:

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including but not limited to hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In certain aspects a prodrug form of the agent or compound may be administered to an individual in need thereof. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The compounds of Formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula I can be determined by comparing their in vitro activity, and in vivo activity in animal models. Such comparison can be done against an established analgesic drug, such as acetaminophen. For example, if a particular compound of Formula 1 is half as active as acetaminophen, then a dosage of approximately twice the established acetaminophen dosage may be appropriate. Conversely, if the compound of Formula 1 is twice as active as acetaminophen, then a dosage of half the established acetaminophen dosage can be used.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will often be in the range of from about 0.15 to about 100 mg/kg, e.g., from about 1 to about 75 mg/kg of body weight per day, such as 0.75 to about 50 mg per kilogram body weight of the recipient per day, preferably in the range of 1 to 90 mg/kg/day, most preferably in the range of 1 to 60 mg/kg/day.

The compound is conveniently administered in unit dosage form; for example, containing 1 to 2000 mg, conveniently 10 to 1000 mg, most conveniently, 5 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Drugs:

The various compounds of Formula 1 can be administered alone or in combination with other drugs. A particularly preferred combination is a compound of Formula 1 in combination with an opioid analgesic. Any of the known opioid analgesics can be combined with a compound of Formula 1. As nonlimiting examples, such analgesics include morphine, codeine, hydrocodone, oxycodone, and hydromorphone.

By way of example, an orally available dosage form of a combination of an opioid drug with a compound of Formula 1 may include from about 20 to about 1000 mg of a compound of Formula 1 in a unit dosage form that also includes one of the following exemplarly opioids: 1-20 mg hydrocodone (such as hydrocodone bitartrate), preferably 2.5 mg, 5 mg, 7.5 mg or 10 mg of hydrocodone or salt thereof; or 1-20 mg oxycodone, preferably 2.5 mg, 5 mg, 7.5 mg or 10 mg of hydrocodone or salt thereof (such as the hydrochloride salt).

Other combinations include combination of a compound of Formula 1 with butalbital, codeine, dihydrocodeine, ibuprofen, aspirin, or naproxen. Administration of any of the combination drugs can be done using the same routes and protocols as described above for compounds of Formula 1.

Methods of Treatment:

The compounds of Formula 1 can be used alone or in any of the foregoing combinations with opioids or other drugs to treat a disease or condition (other than inflammation) that is responsive to an NSAID or any condition responsive to acetaminophen (e.g., pain and/or fever). In one embodiment, the invention provides a method of treating such a disease or condition comprising administering to an individual an effective amount of a compound of Formula 1 alone or as a combination. In some embodiments, the individual is at risk of developing a disease or condition that is responsive to acetaminophen. In some embodiments, methods of treating pain, fever, inflammation, ischemic injury (such as myocardial and/or cerebral), or neuronal injury in an individual, comprising administering to the individual an effective amount of a compound of Formula 1 or combination thereof are provided. In one variation, the individual is post-operative and has or is believed to have or has actually developed post-operative pain. In one variation, the drug or drug combination is administered prophylactically for post-operative pain.

Some embodiments embrace methods of treating pain of any etiology, including acute and chronic pain, and any pain in which acetaminophen analgesic is prescribed. Examples of pain include post-surgical pain, post-operative pain (including dental pain), migraine, headache and trigeminal neuralgia, pain associated with burn, wound or kidney stone, pain associated with trauma (including traumatic head injury), neuropathic pain (e.g., peripheral neuropathy and post-herpetic neuralgia), pain associated with musculo-skeletal disorders, strains, sprains, contusions, fractures, such as myalgia, rheumatoid arthritis, osteoarthritis, cystitis, pancreatitis, inflammatory bowel disease, ankylosing spondylitis, sero-negative (non-rheumatoid) arthropathies, non-articular rheumatism and peri-articular disorders, and pain associated with cancer (including "break-through pain" and pain associated with terminal cancer). Examples of pain with an inflammatory component (in addition to some of those described above) include rheumatic pain, pain associated with mucositis, and dysmenorrhea. In some variations, the methods and formulations of the present invention are used for treatment or prevention of post-surgical pain and/or cancer pain. In some variations, the methods and compositions of the present invention are used for treatment or prevention of pain that is selected from the group consisting of pain associated with surgery, trauma, osteoarthritis, rheumatoid arthritis, lower back pain, fibromyalgia, postherpetic neuralgia, diabetic neuropathy, HIV-associated neuropathy and complex regional pain syndrome.

In some variations, the compounds of Formula 1 are used alone or in combination for treatment or prevention of pain and/or fever (e.g., in adults, children and/or infants). In some embodiments, they are used for treatment of pain, such as acute pain (e.g., acute pain following surgery, such as orthopedic surgery of adults, children, and/or infants). In some embodiments, they are used for treatment or prevention of fever, such as endotoxin-induced fever (e.g., endotoxin-induced fever in adults, children, and/or infants). In some embodiments, they are used for treatment or prevention of fever in children and/or infants. In some embodiments, the fever is selected from low-grade fever, moderate fever, high-grade fever and hyperpyrexia fever. In some embodiments, the fever is selected from Pel-Ebstein fever, continuous fever, intermittent fever, and remittent fever.

In some embodiments, the methods include delaying the onset of analgesia in an individual in need thereof, wherein the method comprises administering to the individual an effective amount of a prodrug of Formula 1 that (in comparison to the parent drug) delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours.

In any of the foregoing methods, administration by injection or infusion represents a preferred technique, and intravenous administration over the course of 1 minute, 5 minutes, 10 minutes, 30 minutes, 1 hour, 2 hours, 6 hours, 12 hours, 24 hours or longer, or any intermediate time, is particularly preferred. Such administration can, in some circumstances, substitute for or significantly reduce the need for administration of opiates, and is of significant benefit in pain management in hospitals or other care facilities. One particular method comprises intravenous administration to an individual in need thereof to manage post-operative or other acute or chronic pain, in either a bolus dose or by infusion over minutes, hours, or days.

Another method is a selecting a therapy for managing or treating pain in an individual in need thereof, comprising evaluating whether the individual is at risk for hepatic toxicity from pain therapy, and selecting therapy with a compound of Formula 1 to reduce or eliminate such risk. The method can further include administering the selected therapy with a compound of Formula 1 to the individual.

Yet another method is a method for providing combination pain therapy. Combinations of a compound of Formula 1 and an opioid analgesic can synergistically relieve pain. The can result in reduction in opioid use. Thus, the method may include managing, treating, or reducing pain by administering an effective amount of a combination of a compound of Formula 1 and an opioid analgesic to a patient. A related method is a method for reducing opioid use in pain management, by selecting and/or administering an amount of a compound of Formula 1 in combination with an amount of an opioid analgesic, wherein the combination provides significantly more pain relief than the amount of either compound alone.

The disclosure can be further understood with reference to the following nonlimiting Examples.

EXAMPLE 1

Preparation of
N-(3-hydroxybicyclo[1.1.1]pentan-1-yl)acetamide
(1)

Step 1. To a solution of 3-aminobicyclo[1.1.1]pentane-1-carboxylic acid (1 mmol) in anhydrous THF (2 mL) at 0° C. under nitrogen is added a methyllithium (1.4 M in diethyl ether, 4 mmol) in a dropwise manner. After addition, the reaction mixture is slowly allowed to warm to room temperature, stirred overnight, and treated with aqueous saturated ammonium chloride solution (4 mL). Ethyl acetate (2 mL) is added and organic layer are separated. The aqueous layer is extracted with ethyl acetate (3×1 mL). The combined organic layers are dried ($Mg_2SO_4$) and concentrated. The residue is purified by a flash chromatography on silica gel (EtOAc/hexnaes) to give 1-(3-aminobicyclo[1.1.1]pentan-1-yl)ethanone.

Step 2. A solution of 1-(3-aminobicyclo[1.1.1]pentan-1-yl)ethanone (1 mmol) in 0.5 mL of chloroform is added to a stirred mixture of m-chloroperbenzoic acid (1.5 mmol) in 2 mL of chloroform at room temperature. The solution is stirred in the dark for 24 h. The mixture is filtered, and the filtrate is washed with 10% sodium bicarbonate and then water. The organic layer is dried over magnesium sulfate and concentrated. The residue is purified by a flash chromatography on silica gel (EtOAc/hexnaes) to give 3-aminobicyclo [1.1.1]pentan-1-yl acetate.

Step 3: To a DMF (2 mL) solution of 3-aminobicyclo [1.1.1]pentan-1-yl acetate (1 mmol) is added sodium bicarbonate (3 mmol) and then acetyl chloride (1 mmol) by syringe at 0° C. The reaction is allowed to warm up to room temperature and monitored by LCMS. After LCMS analysis indicated consumption of starting material, the reaction is diluted with water and extracted with EtOAc (3×). The organic layers are combined, washed with brine, dried (magnesium sulfate), filtered, and concentrated. The crude residue is subjected to flash chromatography (silica gel, EtOAc/hexanes) to give 3-acetamidobicyclo[1.1.1]pentan-1-yl acetate (3).

Step 4: To a THF (2 mL) solution of 3-acetamidobicyclo [1.1.1]pentan-1-yl acetate (3) (1 mmol) is added methanol (0.7 mL) followed by a aqueous solution of NaOH (1.4 M, 0.7 mL, 1 eq) at room temperature. The mixture is stirred and monitored by TLC. After complete consumption of the starting material, saturated ammonium chloride is added and the mixture is stirred for 5 min. The volatiles are removed under vacuum and the resultant mixture is extracted with EtOAc (3×). The organic layers are combined, dried (magnesium sulfate), filtered, and concentrated. The crude residue is subjected to flash chromatography (silica gel, EtOAc/hexanes) to give N-(3-hydroxybicyclo[1.1.1]pentan-1-yl)acetamide (1).

EXAMPLE 2

Preparation of N-(3-ethoxybicyclo[1.1.1]pentan-1-yl)acetamide (2)

2

To a anhydrous THF (5 mL) solution of N-(3-hydroxybicyclo[1.1.1]pentan-1-yl)acetamide (1) (1 mmol) is added NaH (60% dispersion in mineral oil, 3 mmol) portionwise at 0° C. After addition, the mixture is stirred until the evolution of gas stops. Iodoethane (1 mmol) is then added by syringe slowly. The reaction is monitored by LCMS and TLC. After consumption of starting material, the reaction mixture is quenched by adding water (3 mL) and extracted with ethyl acetate (3×). The organic layers are combined, dried (magnesium sulfate), filtered, and concentrated. The crude residue is subjected to flash chromatography (silica gel, EtOAc/hexanes) to afford N-(3-ethoxybicyclo[1.1.1]pentan-1-yl)acetamide (2).

EXAMPLE 3

Preparation of 3-acetamidobicyclo[1.1.1]pentan-1-yl acetate (3)

3

The general procedure of Example 1 is repeated to Step 3, to produce 3-acetamidobicyclo[1.1.1]pentan-1-yl acetate (3).

EXAMPLE 4

Preparation of N-(bicyclo[1.1.1]pentan-1-yl)acetamide (4)

4

To a DMF (12.62 mL) solution of bicyclo[1.1.1]pentan-1-amine, HCl (604 mg, 5.05 mmol) was added sodium bicarbonate (1.272 g, 15.14 mmol) and then acetyl chloride (0.359 mL, 5.05 mmol) by syringe at 0° C. The reaction was allowed to warm up to room temperature and monitored by LCMS. After LCMS analysis indicated consumption of starting material, the reaction was diluted with water and extracted with EtOAc (3×). The organic layers were combined, washed with brine and then dried (magnesium sulfate), filtered, and concentrated. The crude residue was subjected to flash chromatography (silica gel, 0-100% EtOAc/hexanes) to give N-(bicyclo[1.1.1]pentan-1-yl)acetamide (4), as a white solid. MH+=126.2. $^1$H NMR (CDCl$_3$) ppm: 1.91 (s, 3H), 2.06 (s, 6H), 2.42 (s, 1H), 5.88 (br s, 1H).

EXAMPLE 5

Preparation of N-(3-hydroxybicyclo[1.1.1]pentan-1-yl)-N-methylacetamide (5)

5

Step 1: To an anhydrous DMF (5 mL) solution of 3-aminobicyclo[1.1.1]pentan-1-yl acetate (1 mmol; prepared as described in Example 1, Step 2) is potassium carbonate (3 mmol) followed by the addition of methyl iodide (1 mmol) by syringe at room temperature. The reaction is monitored by LCMS and TLC. After consumption of starting material, the reaction mixture is quenched by adding water (3 mL) and extracted with ethyl acetate (3×). The organic layers are combined, dried (magnesium sulfate), filtered, and concentrated. The crude residue is subjected to flash chromatography (silica gel, EtOAc/hexanes) to afford 3-(methylamino)bicyclo[1.1.1]pentan-1-yl acetate.

Step 2: To a THF (2 mL) solution of 3-acetamidobicyclo[1.1.1]pentan-1-yl acetate (3) (1 mmol) is added methanol (0.7 mL) followed by a aqueous solution of NaOH (4 M, 0.7 mL, 3 eq) at room temperature. The mixture is stirred and monitored by TLC. After complete consumption of the starting material, saturated ammonium chloride (3 mL) is added and the mixture is stirred for 5 min. The volatiles are removed under vacuum and the resultant mixture is extracted with EtOAc (3×). The organic layers are combined, dried (magnesium sulfate), filtered, and concentrated. The crude residue is subjected to flash chromatography (silica gel, EtOAc/hexanes) to give 3-(methylamino)bicyclo[1.1.1]pentan-1-ol.

Step 3: The general procedure of Example 1 Step 3 is repeated starting with 3-(methylamino)bicyclo[1.1.1]pentan-1-ol to produce N-(3-hydroxybicyclo[1.1.1]pentan-1-yl)-N-methylacetamide (5).

EXAMPLE 6

Preparation of 3-ethoxybicyclo[1.1.1]pentan-1-amine (6)

6

The general procedure of Example 5 Step 2 is repeated starting with N-(3-ethoxybicyclo[1.1.1]pentan-1-yl)acetamide (2) to produce 3-ethoxybicyclo[1.1.1]pentan-1-amine (6).

EXAMPLE 7

Preparation of 2,2,2-trifluoro-N-(3-hydroxybicyclo[1.1.1]pentan-1-yl)acetamide (7)

7

The general procedure of Example 1 Step 3 is repeated starting with 3-(methylamino)bicyclo[1.1.1]pentan-1-ol and using trifluoroacetic anhydride in place of the acetyl chloride to produce 2,2,2-trifluoro-N-(3-hydroxybicyclo[1.1.1]pentan-1-yl)acetamide (7).

EXAMPLE 8

Preparation of 3-acetamidobicyclo[1.1.1]pentan-1-yl 2-acetoxybenzoate

8

The general procedure of Example 1 Step 3 is repeated starting with N-(3-hydroxybicyclo[1.1.1]pentan-1-yl)acetamide (1) and using O-acetylsalicyloyl chloride in place of the acetyl chloride to produce 3-acetamidobicyclo[1.1.1]pentan-1-yl 2-acetoxybenzoate (8).

EXAMPLE 9

Preparation of 3-acetamidobicyclo[1.1.1]pentan-1-yl 2-(4-isobutylphenyl)propanoate (9)

9

The general procedure of Example 1 Step 3 is repeated starting with N-(3-hydroxybicyclo[1.1.1]pentan-1-yl)acetamide (1) and using 2-(4-isobutylphenyl)propanoyl chloride in place of the acetyl chloride to produce 3-acetamidobicyclo[1.1.1]pentan-1-yl 2-(4-isobutylphenyl)propanoate (9).

What is claimed is:

1. A compound of Formula 1:

Formula 1

$$R^3 \text{---} \text{---} NR^1R^2$$

wherein
$R^1$ is H, —CH$_3$, CF$_3$, or a substituted or unsubstituted (C$_2$ to C$_5$) lower alkyl;
$R^2$ is C(=Y)R$^4$;
$R^3$ is (C$_1$ to C$_{30}$) substituted or unsubstituted alkyl, alkenyl, cycloalkyl, cycloalkenyl, cycloalkynyl, heterocycle, heteroaryl, arylalkyl, alkylaryl or heteroarylalkyl;
$R^4$ is (C$_1$ to C$_{10}$) substituted or unsubstituted lower alkyl; and
Y is O.

2. The compound of claim 1, wherein $R^1$ is H.
3. The compound of claim 1, wherein $R^1$ is —CH$_3$.
4. The compound of claim 1, wherein $R^2$ is C(=Y)R$^4$.
5. The compound of claim 1, wherein $R^3$ is (C$_1$ to C$_{30}$) substituted alkyl.
6. The compound of claim 1, wherein $R^3$ is (C$_1$ to C$_{30}$) unsubstituted alkyl.
7. The compound of claim 1, wherein $R^3$ is alkenyl.
8. The compound of claim 1, wherein $R^3$ is cycloalkyl.
9. The compound of claim 1, wherein $R^3$ is cycloalkenyl.
10. The compound of claim 1, wherein $R^3$ is heterocycle.
11. The compound of claim 1, wherein $R^3$ is heteroaryl.
12. The compound of claim 1, wherein $R^3$ is arylalkyl.
13. The compound of claim 1, wherein $R^3$ is heteroarylalkyl.

* * * * *